United States Patent
Bates et al.

(10) Patent No.: US 6,899,519 B2
(45) Date of Patent: May 31, 2005

(54) METHOD OF DETECTING A CHANGE IN THE STRUCTURE OF A COMPLEX SHAPE ARTICLE

(75) Inventors: Jonathan G Bates, Derby (GB); John R Webster, Derby (GB)

(73) Assignee: Rolls-Royce plc, London (GB)

( * ) Notice: Subject to any disclaimer, the term of this patent is extended or adjusted under 35 U.S.C. 154(b) by 7 days.

(21) Appl. No.: 10/391,751

(22) Filed: Mar. 20, 2003

(65) Prior Publication Data

US 2004/0009065 A1 Jan. 15, 2004

(30) Foreign Application Priority Data

Mar. 28, 2002 (GB) .............................. 0207322

(51) Int. Cl.$^7$ .............................................. F01B 25/26
(52) U.S. Cl. ................... 415/118; 415/119; 416/198 A; 416/201 R; 416/61; 416/31
(58) Field of Search .................. 416/198 A, 201 R, 416/61, 31, 1; 415/119, 118; 73/583, 597

(56) References Cited

U.S. PATENT DOCUMENTS 2,966,058 A * 12/1960 McSkimin ................... 73/597
3,923,415 A * 12/1975 Benedict ....................... 415/1
3,978,712 A * 9/1976 Cowan et al. ................ 73/597
5,507,183 A 4/1996 Larue et al.
5,942,690 A * 8/1999 Shvetsky ..................... 73/593

FOREIGN PATENT DOCUMENTS

GB 2366382 A 3/2002

* cited by examiner

Primary Examiner—Theresa Trieu
(74) Attorney, Agent, or Firm—W. Warren Taltavull; Manelli Denison & Selter PLLC

(57) ABSTRACT

A method of detecting the change in the structure of a turbine rotor uses the steps of injecting an ultrasonic signal into the turbine rotor at a first position using a first ultrasonic transducer to produce a diffuse field ultrasonic signal in the rotor; detecting the signal in the rotor at a second position using a second ultrasonic transducer measuring the time for the signal to travel from the first ultrasonic transducer to the second ultrasonic transducer and comparing the measured time for the diffuse field ultrasonic signal to travel from the first ultrasonic transducer to the second ultrasonic transducer with a stored time for the diffuse field ultrasonic signal to travel from the first ultrasonic transducer to the second ultrasonic transducer to determine if there is a change in the structure of the turbine rotor.

22 Claims, 4 Drawing Sheets

METHOD OF DETECTING A CHANGE IN THE STRUCTURE OF A COMPLEX SHAPE ARTICLE

FIELD OF THE INVENTION

The present invention relates to a method of detecting a change in the structure of a complex shape article. The present invention relates in particular to a method of detecting a change in the structure of a rotor, in particular the structure of a turbine rotor.

BACKGROUND OF THE INVENTION

In some gas turbine engines a turbine rotor comprises a plurality of axially spaced turbine discs. The turbine discs are fastened together at a first radially inner position by a plurality of axially extending bolts, which extend through axially extending projections on the turbine discs, and associated nuts. The turbine discs have axially extending sealing members to define seals at a second radially outer position.

A problem with this turbine rotor is that if the turbine discs are not clamped, or fastened, together sufficiently tightly there is a significant axial gap between the axially extending sealing members and this allows the turbine rotor and hence the gas turbine engine to vibrate. Additionally, if the sealing members are machined out of tolerance, or if the sealing members are worn, there may be a significant axial gap between the axially extending sealing members and this allows the turbine rotor and hence the gas turbine engine to vibrate.

Thus there is a need to ensure that the there is no gap, or substantially no gap, between the sealing members so as to reduce the vibration of the turbine rotor.

It is known to detect defects, cracks or flaws, in articles by injecting a coherent high frequency, over 1 MHz, ultrasonic signal into the article and detecting the reflection of the coherent high frequency ultrasonic signal from the defect. By measuring the time for the high frequency ultrasonic signal to travel from the point of injection to the defect and back the location of the defect is determined.

SUMMARY OF THE INVENTION

Accordingly the present invention seeks to provide a novel method of detecting a change in the structure of a complex shape article, which reduces, preferably overcomes, the above-mentioned problems.

Accordingly the present invention provides a method of detecting a change in the structure of a complex shape article comprising injecting an ultrasonic signal into the complex shape article at a first position to produce a diffuse field ultrasonic signal in the complex shape article, detecting the diffuse field ultrasonic signal in the complex shape article at a second position, measuring the time for the diffuse field ultrasonic signal to travel from the first position to the second position, comparing the measured time for the diffuse field ultrasonic signal to travel from the first position to the second position with a stored time for the diffuse field ultrasonic signal to travel from the first position to the second position, and determining if there is a change in the time for the diffuse field ultrasonic signal to travel from the first position to the second position, which is indicative of a change in the structure of the complex shape article.

Preferably the complex shape article comprises a rotor comprising a plurality of axially spaced rotor discs, the axially spaced rotor discs being acoustically connected by a plurality of propagation paths.

Preferably the rotor is a turbine rotor comprising a plurality of axially spaced turbine discs.

Preferably at least one of the propagation paths comprises at least one axially extending fastener to secure the rotor discs together. Preferably the at least one of the propagation paths comprises at least one projection extending axially from at least one of the rotor discs, the fastener extending axially through the at least one projection, the at least one projection abutting an adjacent rotor disc.

Preferably at least one of the propagation paths comprises at least one member extending axially from at least one of the rotor discs towards an adjacent rotor disc.

Preferably the detecting of change in the structure of the rotor comprises detecting a change in the number of propagation paths acoustically connecting the rotor discs.

Preferably the detecting of change in the structure of the rotor comprises detecting a change in the length of shortest propagation path acoustically connecting the rotor discs.

Preferably the detecting of change in the structure of the complex shape article comprises detecting a change in the length of shortest propagation path acoustically connecting the first and second positions.

Preferably the method comprises injecting the ultrasonic signal into a first one of the rotors at a first position to produce a diffuse field ultrasonic signal in the rotor and detecting the diffuse field ultrasonic signal in a second one of the rotor discs at a second position.

Preferably the axially extending member and the axially extending projection are at different radial positions on the rotor.

Preferably the axially extending member is an annular seal.

Preferably the ultrasonic signal has a frequency in the range 40 kHz to 1 MHz. Preferably the ultrasonic signal has a frequency of about 300 kHz.

The method may comprise detecting the presence, or absence, of a sealing element on the article or detecting the presence, or absence, of a bond between parts of the article or detecting the presence, or absence, of a fluid or contaminant in contact with the article.

The present invention also provides an apparatus for detecting the change in the structure of a complex shape article comprising a first transducer for injecting an ultrasonic signal into the complex shape article at a first position to produce a diffuse field ultrasonic signal in the complex shape article, a second transducer for detecting the diffuse field ultrasonic signal in the complex shape article at a second position, means to measure the time for the diffuse field ultrasonic signal to travel from the first position to the second position, means to compare the measured time for the diffuse field ultrasonic signal to travel from the first position to the second position with a stored time for the diffuse field ultrasonic signal to travel from the first position to the second position, and means to determine if there is a change in the time for the diffuse field ultrasonic signal to travel from the first position to the second position, which is indicative of a change in the structure of the complex shape article.

BRIEF DESCRIPTION OF THE DRAWINGS

The present invention will be more fully described by way of example with reference to the accompanying drawings in which.

DETAILED DESCRIPTION OF THE INVENTION

Figure 1:
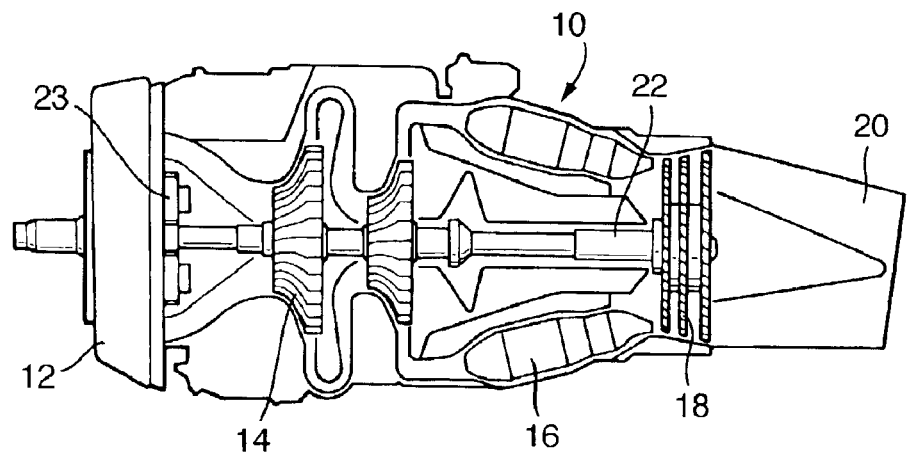
FIG. 1 shows a gas turbine engine having a turbine rotor.

A turboprop gas turbine engine 10, as shown in FIG. 1, comprises an intake 12, a compressor section 14, a combustion section 16, a turbine section 18 and an exhaust 20. The turbine section 18 is arranged to drive the compressor section 14 via a shaft 22 and the turbine section 18 is arranged to drive a propeller (not shown) via the shaft 22 and a gearbox 23. The operation of the gas turbine engine 10 is quite conventional and will not be discussed further.

Figure 2:
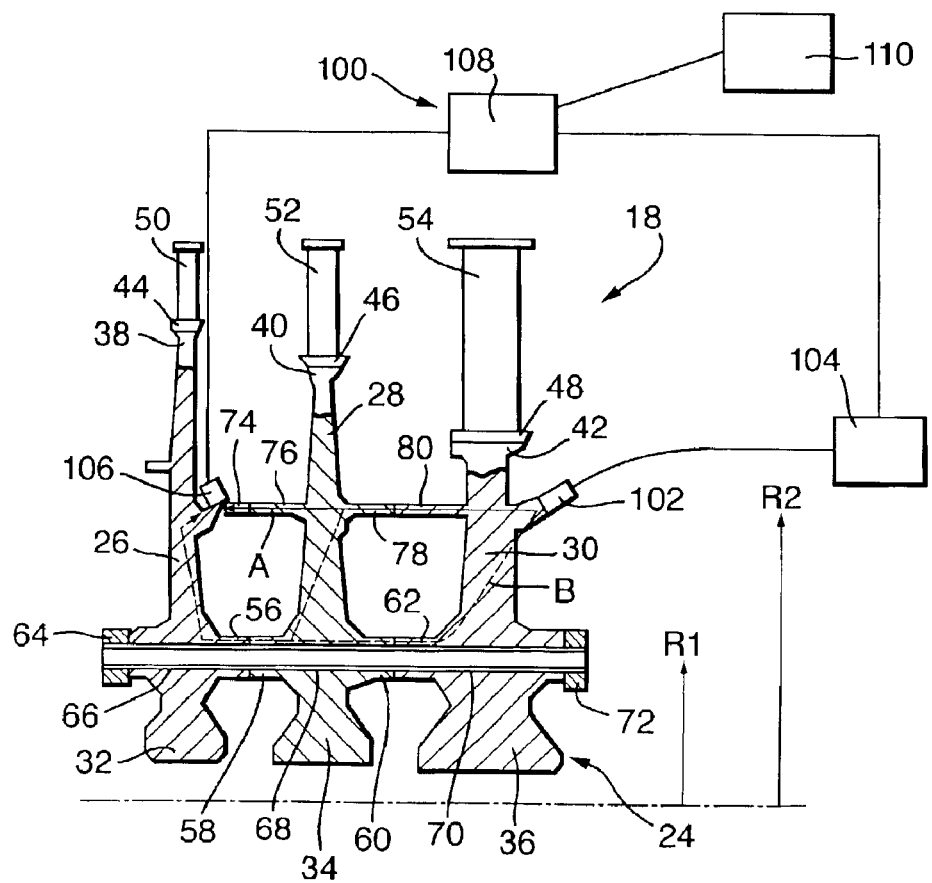
FIG. 2 shows an apparatus for detecting a change in the structure of the turbine rotor according to the present invention.

The turbine section 18, as shown more clearly in FIG. 2, comprises a turbine rotor 24, which comprises a plurality of, in this example three, axially spaced turbine discs 26, 28 and 30. The turbine discs 26, 28 and 30 have cobs 32, 34 and 36 respectively at their radially inner ends and rims 38, 40 and 42 respectively at their radially outer ends. The rims 38, 40 and 42 are provided with a plurality of circumferentially spaced axially extending slots 44, 46 and 48 respectively to receive a plurality of turbine blades 50, 52 and 54 respectively.

The turbine disc 26 has a plurality of circumferentially spaced axially extending projections 56 extending axially towards the turbine disc 28. The turbine disc 28 has a plurality of circumferentially spaced axially extending projections 58 extending axially towards and abutting the respective projections 56 on the turbine disc 26. The turbine disc 28 also has a plurality of circumferentially spaced axially extending projections 60 extending axially towards the turbine disc 30. The turbine disc 30 has a plurality of circumferentially spaced axially extending projections 62 extending axially towards and abutting the respective projections 60 on the turbine disc 28. The turbine discs 26, 28 and 30 are fastened together by a plurality of circumferentially spaced axially extending bolts 64 which extend through apertures 66, 68 and 70 in the turbine discs 26, 28 and 30 respectively and associated nuts 72. The apertures 66, 68 and 70 also extend through the projections 56, 58, 60 and 62 of the turbine discs 26, 28 and 30. The bolts 64, apertures 66, 68 and 70 and projections 56, 58, 60 and 62 are arranged at a common radius R1 from the axis of the turbine rotor 24.

The turbine disc 26 has an axially extending annular sealing member 74 extending axially towards the turbine disc 28. The turbine disc 28 has an axially extending annular sealing member 76 extending axially towards and abutting annular sealing member 74 on the turbine disc 26. The turbine disc 28 also has an axially extending annular sealing member 78 extending axially towards the turbine disc 30. The turbine disc 30 has an axially extending annular sealing member 80 extending axially towards and abutting annular sealing member 78 on the turbine disc 28. The annular sealing members 74, 76, 78 and 80 are arranged at a common radius R2 from the axis of the turbine rotor 24, where R2 is greater than R1.

As mentioned previously if the bolts 64 and nuts 72 are not tightened sufficiently to clamp the turbine discs 26, 28 and 30 together, if the sealing members 74, 76, 78 and 80 are worn or if the sealing members 74, 76, 78 and 80 are not machined to tolerance, then gaps, or clearances, are formed between the annular sealing members 74 and 76 and between the annular sealing members 78 and 80. This allows undesirable vibration of the turbine rotor 24 in operation.

An apparatus 100, as shown in FIG. 2, for detecting a change in the structure of the turbine rotor 24 comprises a first ultrasonic transducer 102 for injecting an ultrasonic signal into the turbine rotor 24 located at a first position to produce a diffuse field ultrasonic signal in the turbine rotor 24. In particular the first ultrasonic transducer 102 is located on, and acoustically coupled to, the turbine disc 30 substantially at the radius R2. A pulse generator 104 supplies electrical pulses to the first ultrasonic transducer 102, which converts the electrical pulses into ultrasonic pulses.

A second ultrasonic transducer 106 for detecting the diffuse field ultrasonic signal in the turbine rotor 24 is located at a second position. In particular the second ultrasonic transducer 106 is located on, and acoustically coupled to, the turbine disc 26 substantially at the radius R2. The second ultrasonic transducer 106 supplies an electrical signal corresponding to the diffuse field ultrasonic signal to a processor means 108. The first ultrasonic transducer 102 also supplies an electrical signal to the processor means 108.

The processor means 108 is arranged to measure the time for the diffuse field ultrasonic signal to travel from the first position to the second position using the electrical signals supplied by the first and second ultrasonic transducers 102 and 106. The processor means 108 is also arranged to compare the measured time for the diffuse field ultrasonic signal to travel from the first position to the second position with a stored time for the diffuse field ultrasonic signal to travel from the first position to the second position. The processor means 108 thus determines if there is a change in the structure of the turbine rotor 24. The processor means 108 provides a signal to a display 110 to indicate that the structure of the turbine rotor 24 has, or has not, changed. The processor 108 may simply display the travel time on the display 110.

If the bolts 64 and nuts 72 are sufficiently tight to clamp the turbine discs 26, 28 and 30 securely, if the sealing members 74, 76, 78 and 80 are not worn and if the sealing members 74, 76, 78 and 80 are machined to tolerance then the annular sealing members 74, 76, 78 and 80 abut each other and there is a direct propagation path A for the diffuse field ultrasonic signal acoustically connecting the first transducer 102 to the second transducer 106 through the turbine disc 30, the annular sealing member 80, the annular sealing member 78, the turbine disc 28, the annular sealing member 76, the annular sealing member 74 and the turbine disc 26. There is also an indirect acoustic propagation path B for the diffuse field ultrasonic signal acoustically connecting the first transducer 102 to the second transducer 106 through the turbine disc 30, the projections 62, the projections 60, the turbine disc 28, the projections 58, the projections 56 and the turbine disc 26.

Figure 4:
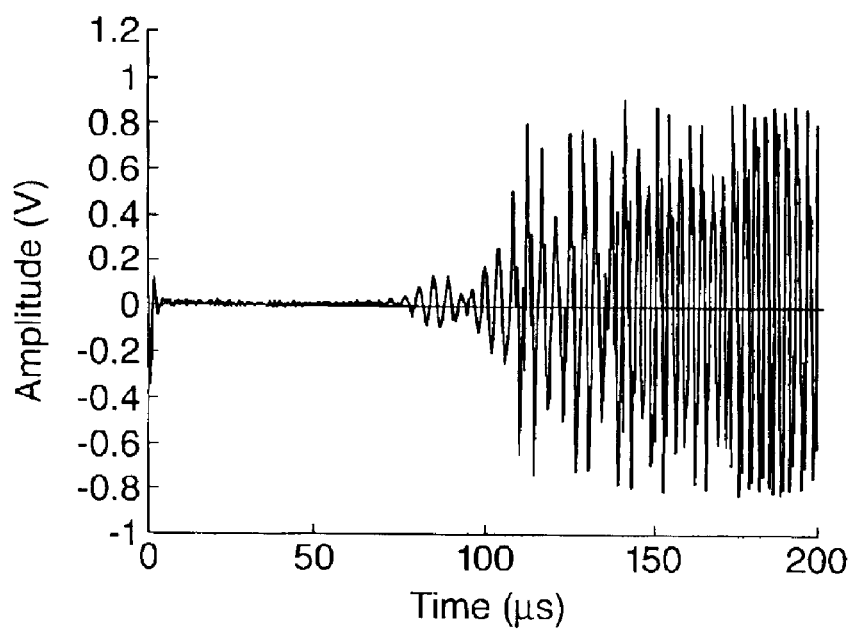
FIG. 4 is a graph showing the amplitude of a detected diffuse field ultrasonic signal with time for a turbine rotor with satisfactory clamping of the turbine discs.

FIG. 4 shows the ultrasonic signal received by the second transducer 106, which indicates that the time taken for the diffuse field ultrasonic signal to reach the second transducer 106 is about 70 μs to 80 μs.

If the bolts 64 and nuts 72 are insufficiently tight to clamp the turbine discs 26, 28 and 30 securely, if the sealing members 74, 76, 78 and 80 are worn or if the sealing members 74, 76, 78 and 80 are not machined to tolerance then the annular sealing members 74, 76, 78 and 80 do not abut each other and there are gaps such that there is no direct propagation path A for the diffuse field ultrasonic signal from the first transducer 102 to the second transducer 106 through the turbine disc 30, the annular sealing member 80, the annular sealing member 78, the turbine disc 28, the annular sealing member 76, the annular sealing member 74 and the turbine disc 26. However, there is an indirect propagation path B for the diffuse field ultrasonic signal acoustically connecting the first transducer 102 to the second transducer 106 through the turbine disc 30, the projections 62, the projections 60, the turbine disc 28, the projections 58, the projections 56 and the turbine disc 26.

Figure 5:
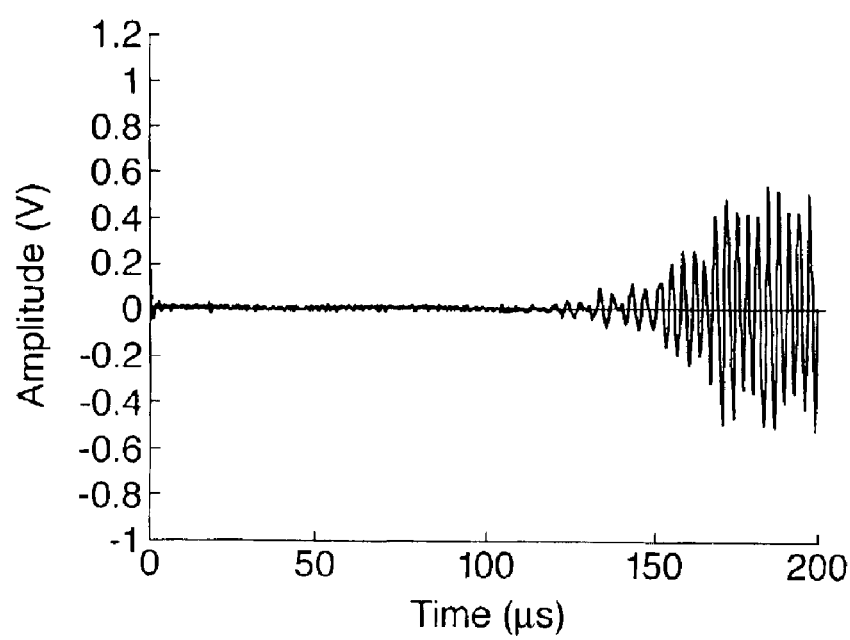
FIG. 5 is a graph showing the amplitude of a detected diffuse field ultrasonic signal with time for a turbine rotor with unsatisfactory clamping of the turbine discs.

FIG. 5 shows the ultrasonic signal received by the second transducer 106, which indicates that the time taken for the diffuse field ultrasonic signal to reach the second transducer 106 is about 120 $\mu$s to 130 $\mu$s.

Thus the apparatus 100 detects a change in the number of propagation paths connecting the rotor discs 26, 28 and 30 or detects a change in the length of the shortest propagation path connecting the rotor discs 26, 28 and 30. In one case the shortest propagation path is path A and in one case the shortest propagation path is path B.

Thus it is then possible to tighten the bolts 64 and nuts 72, machine the projections 56, 58, 60 or 62 or increase the length of the sealing members 74, 76, 78 or 80 to ensure that the sealing members 74, 76, 78 and 80 abut each other to reduce vibrations of the turbine rotor 24.

Figure 3:
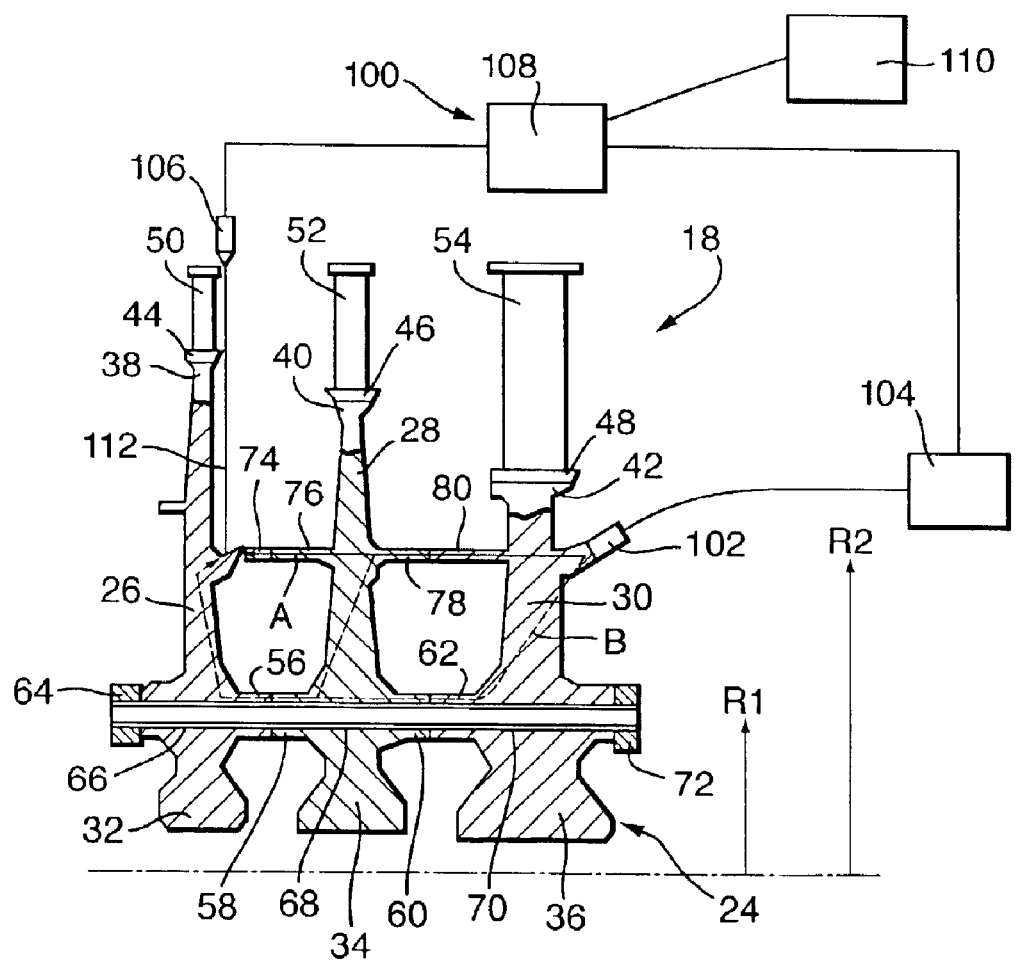
FIG. 3 shows an alternative apparatus for detecting a change in the structure of the turbine rotor according to the present invention.

An alternative arrangement is shown in FIG. 3 in which like parts are denoted by like numerals. FIG. 3 differs in that an acoustic waveguide 112 is used to acoustically couple the second transducer 106 to the turbine disc 26 of the turbine rotor 24. Alternatively, or in addition, an acoustic waveguide may be used to acoustically couple the first transducer 102 to the turbine disc 30 of the turbine rotor 24.

The acoustic waveguide 112 allows the testing to be performed without dismantling of the gas turbine engine 10 if the second ultrasonic transducer 106 or first ultrasonic transducer 102 has to be acoustically coupled to an inaccessible location on the turbine rotor 24. The acoustic waveguide 112 comprises any suitable material, which allows the propagation of the ultrasonic signal, for example stainless steel.

The ultrasonic transducers 102 and 106 are preferably resonant ultrasonic transducers.

The time for the diffuse field ultrasonic signal to travel from the first position to the second position is measured using the time for the amplitude of the diffuse ultrasonic signal to exceed a predetermined amplitude, known as threshold crossing. Alternatively the time for the diffuse field ultrasonic signal to travel from the first position to the second position is measured for a number of results and an average time for the number of results is calculated and a floating threshold that has been determined using statistics of part of the waveform prior to first arrival is used.

The processor comprises a standard wide bandwidth ultrasonic flaw detector for supplying a pulse to the first transducer such that the ultrasonic signal is emitted from the first ultrasonic transducer and the standard wide bandwidth ultrasonic flaw detector is used to display the diffuse field ultrasonic signal detected by the second ultrasonic transducer. However, a high input impedance preamplifier is necessary between the second ultrasonic transducer and the ultrasonic flaw detector to isolate the second ultrasonic transducer from the low impedance input on the ultrasonic flaw detector.

The ultrasonic transducers are arranged to operate at a lower frequency of 300 kHz in order to produce the diffuse field ultrasonic signal in the turbine rotor. The lower frequencies are used in order to allow the ultrasonic signal to travel around corners in complex shape articles. However, the ultrasonic transducers may be arranged to operate at lower frequencies between 40 kHz and 1 MHz, preferably 100 kHz to 500 kHz, depending on the geometry and size of the article. The first ultrasonic transducer injects ultrasonic pulses into the article at a repetition rate of about 20 Hz, in order to allow the diffuse field ultrasonic signal to fully decay before the injection of the next ultrasonic pulse.

Thus in the present invention a relatively low frequency ultrasonic signal is injected into the article. The low frequency ultrasonic signal propagates around the article and eventually reaches all points within the article. The nature, shape, frequency etc and arrival time of the ultrasonic signal depends on the first and second positions and the structure of the article through which the ultrasonic signal has passed. Any change in the structure of the article results in a change of the ultrasonic signal detected by the second transducer. The frequency of the ultrasonic signal is chosen depending on the shape and size of the article and the size of the change in the structure of the article. The positions of the first and second transducers are selected so that the change in the structure produces a change in the travel time for the diffuse field ultrasonic signal.

It may be possible to have a third ultrasonic transducer for detecting the diffuse field ultrasonic signal in the complex shape article at a third position, means to measure the time for the diffuse field ultrasonic signal to travel from the first position to the third position, means to compare the measured time for the diffuse field ultrasonic signal to travel from the first position to the third position with a stored time for the diffuse field ultrasonic signal to travel from the first position to the third position to determine if there is a change in the structure of the complex shape article.

Figure 6:
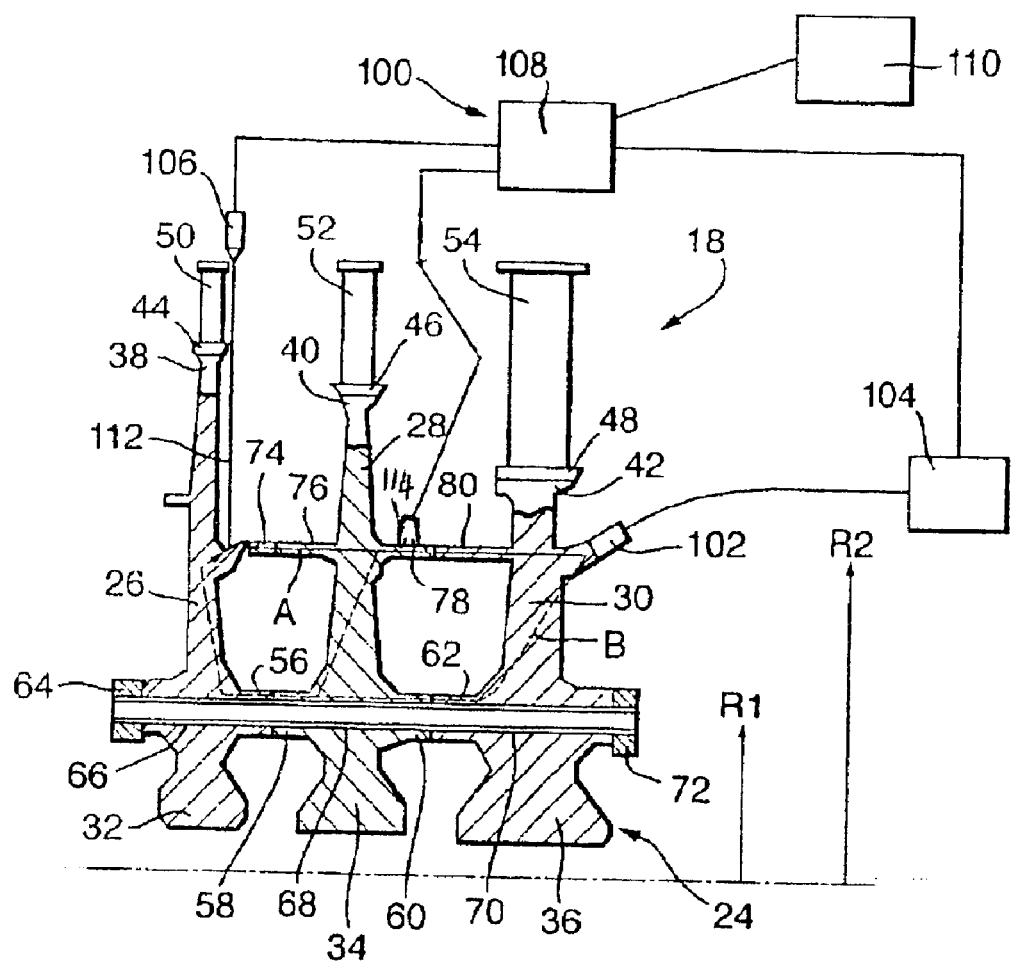
FIG. 6 is a view similar to FIG. 3 but showing the position of a third transducer.

The second and third ultrasonic transducers may be used sequentially or simultaneously. Thus it may be possible to provide a third ultrasonic transducer as shown in FIG. 6 at 114 on the turbine disc 28.

Thus the present invention may be used with a plurality of detecting ultrasonic transducers to detect changes in the structure in different parts of the article.

Although the present invention has been described with reference to a bolted joint connecting the turbine discs, it is equally applicable to turbine discs connected by a welded joint, a diffusion bonded joint or other suitable type of bonded joint or mechanical joint.

Thus the present invention may also be used to detect other changes in the structure of an article, for example an article in which a sealing element, a gasket, has been omitted resulting in a gap, an article in which a weld, or bond, is defective, or omitted, resulting in a gap or an article with loose pipe clips or detecting the presence, or absence, of a fluid or contaminant in contact with the article.

In addition the envelope shape, the differential frequency or the attenuation of the diffuse field ultrasonic signal may be used.

What is claimed is:

1. A method of detecting a change in the structure of a complex shape article comprising the steps of injecting an ultrasonic signal into the complex shape article at a first position to produce a diffuse field ultrasonic signal in the complex shape article, detecting the diffuse field ultrasonic signal in the complex shape article at a second position, measuring the time for the diffuse field ultrasonic signal to travel from the first position to the second position, comparing the measured time for the diffuse field ultrasonic signal to travel from the first position to the second position with a stored time for the diffuse field ultrasonic signal to travel from the first position to the second position, and determining if there is a change in the time for the diffuse field ultrasonic signal to travel from the first position to the second position, which is indicative of a change in the structure of the complex shape article wherein the complex shape article comprises a rotor comprising a plurality of axially spaced rotor discs, the axially spaced rotor discs being acoustically connected by a plurality of propagation paths.

2. A method as claimed in claim 1 wherein the rotor is a turbine rotor comprising a plurality of axially spaced turbine discs.

3. A method as claimed in claim 1 wherein the at least one of the propagation paths comprises at least one axially extending fastener to secure the rotor discs together.

4. A method as claimed in claim 3 wherein the at least one of the propagation paths comprises at least one projection extending axially from at least one of the rotor discs, the fastener extending axially through the at least one projection, the at least one projection abutting an adjacent rotor disc.

5. A method as claimed in claim 1 wherein the at least one of the propagation paths comprises at least one member extending axially from at least one of the rotor discs towards an adjacent rotor disc.

6. A method as claimed in claim 5 wherein the complex shape article comprises a rotor comprising a plurality of axially spaced rotor discs, the axially spaced rotor discs being acoustically connected by a plurality of propagation paths and wherein the at least one of the propagation paths comprises at least one axially extending fastener to secure the rotor discs together and wherein the axially extending member and the axially extending projection are at different radial positions on the rotor.

7. A method as claimed in claim 6 wherein the axially extending member is an annular seal.

8. A method as claimed in claim 5 wherein the axially extending member is an annular seal.

9. A method as claimed in claim 5 wherein the complex shape article comprises a rotor comprising a plurality of axially spaced rotor discs, the axially spaced rotor discs being acoustically connected by a plurality of propagation paths and wherein the at least one of the propagation paths comprises at least one axially extending fastener to secure the rotor discs together and wherein the at least one of the propagation paths comprises at least one projection extending axially from at least one of the rotor discs, the fastener extending axially through the at least one projection, the at least one projection abutting an adjacent rotor disc and wherein the axially extending member and the axially extending projection are at different radial positions on the rotor.

10. A method as claimed in claim 1 wherein the detecting of change in the structure of the rotor comprises detecting a change in the number of propagation paths acoustically connecting the rotor discs.

11. A method as claimed in claim 1 wherein the detecting of change in the structure of the rotor comprises detecting a change in the length of shortest propagation path acoustically connecting the rotor discs.

12. A method as claimed in claim 1 wherein the method comprises injecting the ultrasonic signal into a first one of the rotors at a first position to produce a diffuse field ultrasonic signal in the rotor and detecting the diffuse field ultrasonic signal in a second one of the rotor discs at a second position.

13. The method as claimed in claim 1 comprising detecting the diffuse field ultrasonic signal in the complex shape article at a third position, the time for the diffuse field ultrasonic signal to travel from the first position to the third position, comparing the measured time for the diffuse field ultrasonic signal to travel from the first position to the third position with a stored time for the diffuse field ultrasonic signal to travel from the first position to the third position, and determining if there is a change in the time for the diffuse field ultrasonic signal to travel from the first position to the third position, which is indicative of a change in the structure of the complex shape article.

14. A method as claimed in claim 1 wherein the ultrasonic signal has a frequency in the range of 100 kHz to 500 kHz.

15. A method of detecting a change in the structure of a complex shape article comprising the steps of injecting an ultrasonic signal into the complex shape article at a first position to produce a diffuse field ultrasonic signal in the complex shape article, detecting the diffuse field ultrasonic signal in the complex shape article at a second position, measuring the time for the diffuse field ultrasonic signal to travel from the first position to the second position, comparing the measured time for the diffuse field ultrasonic signal to travel from the first position to the second position with a stored time for the diffuse field ultrasonic signal to travel from the first position to the second position, and determining if there is a change in the time for the diffuse field ultrasonic signal to travel from the first position to the second position, which is indicative of a change in the structure of the complex shape article and comprising detecting the presence, or absence, of a sealing element on the article or detecting the presence, or absence, of a bond between parts of the article.

16. A method as claimed in claim 15 wherein the ultrasonic signal has a frequency in the range 40 kHz to 1 MHz.

17. A method as claimed in claim 15 wherein the ultrasonic signal has a frequency of about 300 kHz.

18. A method as claimed in claim 15 comprising detecting the diffuse field ultrasonic signal in the complex shape article at a third position, the time for the diffuse field ultrasonic signal to travel from the first position to the third position, comparing the measured time for the diffuse field ultrasonic signal to travel from the first position to the third position with a stored time for the diffuse field ultrasonic signal to travel from the first position to the third position, and determining if there is a change in the time for the diffuse field ultrasonic signal to travel from the first position to the third position, which is indicative of a change in the structure of the complex shape article.

19. A method as claimed in claim 15 wherein the ultrasonic signal has a frequency in the range of 100 kHz to 500 kHz.

20. A method as claimed in claim 15 comprising detecting the diffuse field ultrasonic signal in the complex shape article at a third position, the time for the diffuse field ultrasonic signal to travel from the first position to the third position, comparing the measured time for the diffuse field ultrasonic signal to travel from the first position to the third position with a stored time for the diffuse field ultrasonic signal to travel from the first position to the third position, and determining if there is a change in the time for the diffuse field ultrasonic signal to travel from the first position to the third position, which is indicative of a change in the structure of the complex shape article.

21. An apparatus for detecting the change in the structure of a complex shape article comprising a first transducer for injecting an ultrasonic signal into the complex shape article at a first position to produce a diffuse field ultrasonic signal in the complex shape article, a second transducer for detecting the diffuse field ultrasonic signal in the complex shape article at a second position, means for measuring the time for the diffuse field ultrasonic signal to travel from the first position to the second position, means for comparing the measured time for the diffuse field ultrasonic signal to travel from the first position to the second position with a stored time for the diffuse field ultrasonic signal to travel from the first position to the second position, and means for determining if there is a change in the time for the diffuse field ultrasonic signal to travel from the first position to the second position, which is indicative of a change in the structure of the complex shape article wherein the complex shape article comprises a rotor comprising a plurality of axially spaced rotor discs, the axially spaced rotor discs being acoustically connected by a plurality of propagation paths.

22. An apparatus as claimed in claim 21 comprising detecting the diffuse field ultrasonic signal in the complex shape article at a third position, means for measuring the time for the diffuse field ultrasonic signal to travel from the first position to the third position, means for comparing the measured time for the diffuse field ultrasonic signal to travel from the first position to the third position with a stored time for the diffuse field ultrasonic signal to travel from the first position to the third position, and means for determining if there is a change in the time for the diffuse field ultrasonic signal to travel from the first position to the third position, which is indicative of a change in the structure of the complex shape article.

* * * * *